United States Patent

Ketchum

[11] Patent Number: 5,862,804
[45] Date of Patent: Jan. 26, 1999

[54] LEAK POINT WETNESS SENSOR FOR UROLOGICAL INVESTIGATION

[75] Inventor: Gary T. Ketchum, Ojai, Calif.

[73] Assignee: Andco Tek, Inc., Ventura, Calif.

[21] Appl. No.: 889,781

[22] Filed: Jul. 8, 1997

[51] Int. Cl.$^6$ ..................................................... A61F 5/48
[52] U.S. Cl. ........................................... 128/885; 128/886
[58] Field of Search ..................................... 128/885, 886, 128/DIG. 25; 340/539, 573, 604, 620

[56] References Cited

U.S. PATENT DOCUMENTS

| | | | |
|---|---|---|---|
| 3,818,468 | 6/1974 | Toth | 128/886 |
| 4,800,370 | 1/1989 | Vetecnik | 128/886 |
| 5,469,145 | 11/1995 | Johnson | 128/886 |
| 5,709,222 | 1/1998 | Davallou | 128/886 |

*Primary Examiner*—Michael A. Brown
*Attorney, Agent, or Firm*—Donald D. Mon

[57] ABSTRACT

A leakpoint wetness sensor for urological investigations including an instrument having a passage therethrough to pass a catheter intended for insertion into the bladder through the urethra. A temperature sensitive reference sensor mounted to the body and exposed to and responsive to ambient temperature. A receptacle in the body so disposed and arranged to receive liquid which leaks from the urethra past the catheter. A temperature sensitive detector sensor mounted to the body where it will be contacted by the leaked liquid and detector sensor being responsive to the temperature of the liquid. A circuit device is responsive to outputs from the sensors to provide a response reflective of a difference between the temperatures when the detector sensor is wetted by leaked liquid.

10 Claims, 1 Drawing Sheet

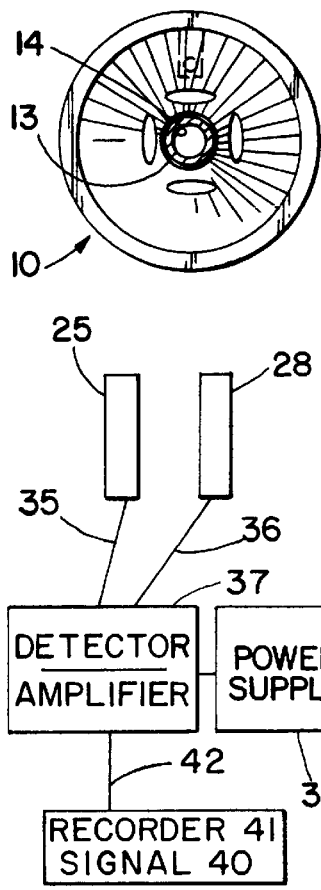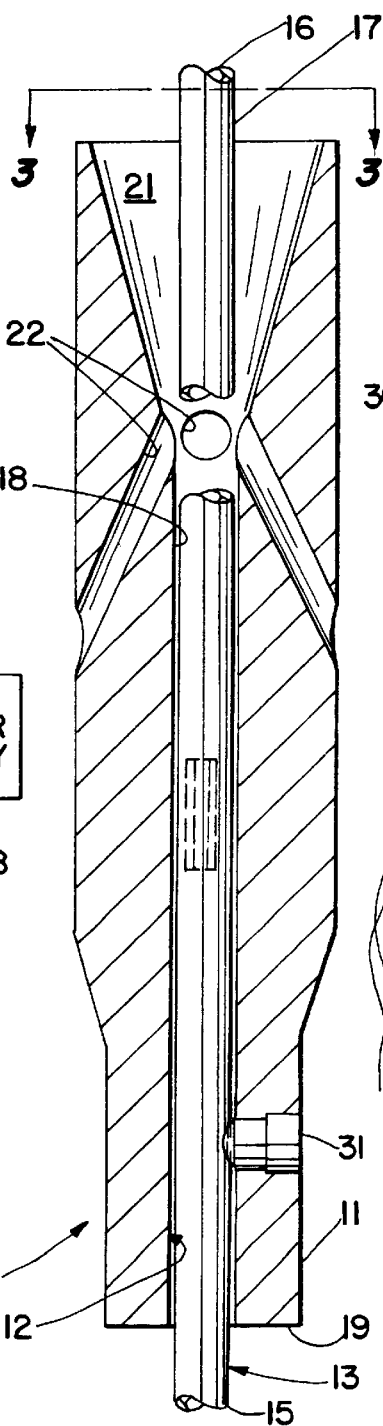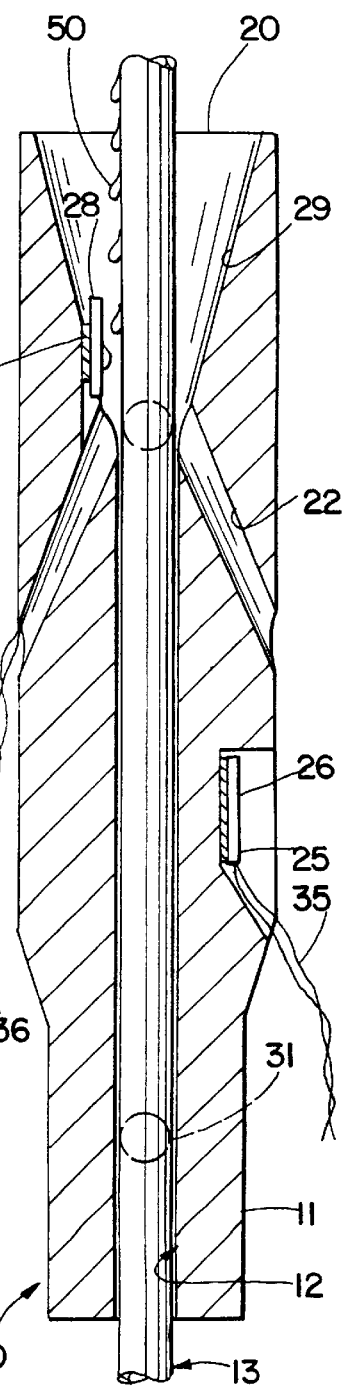

LEAK POINT WETNESS SENSOR FOR UROLOGICAL INVESTIGATION

FIELD OF THE INVENTION

For use in urological investigations of the female bladder and urethra, a detector responsive to leakage of liquid from the urethra.

BACKGROUND OF THE INVENTION

Urologists are interested in learning when and under what conditions leakage from urethra first occurs during an investigation of the bladder and urethra. In the course of the investigation, liquid is forced into the bladder through a catheter, and the pressure and the amount of liquid (urine and water) is known. The patient is asked to assume a number of positions, and to make various exertions, such as muscular contraction and coughing. In the course of these events, liquid will at times and under certain circumstances leak past the catheter. The conditions under which this leakage just begins is of importance to the urologist in his investigation of the bladder and urethra.

While leakage can be visually detected, the relationship of its exact time of occurrence with respect to other measured parameters during a urodynamic procedure is critical for the proper evaluation of the test data. It is an object of this invention to provide a simple and rugged sensor and related circuity which will inform the urologist of the event of leakage, and if desired also record the relative time and conditions under which it occurred, all without immediate attention by the urologist.

BRIEF DESCRIPTION OF THE INVENTION

This invention relies on the fact that liquid from the urethra will not be at room temperature. Leakage is detected by comparing the temperature of the leaked liquid to the room temperature. For this to occur, two temperature-responsive devices, preferably thermistors are provided. One is exposed only to room temperature. The other is placed where leaked liquid will contact it.

When leaked fluid contacts the second thermistor, its higher temperature causes a change in the resistance of the thermistor, which is compared and the fact of the difference in temperature is signaled to the urologist as the event of leakage and if desired also to a recorder.

According to a preferred but optional feature of the invention, circuitry responsive to the difference in temperatures may be adjusted in sensitivity so as not to respond to trivial changes which may not be related to leakage of liquid.

The above and other features of this invention will be fully understood from the following detailed description and the accompanying drawings, in which:

BRIEF DESCRIPTION OF THE DRAWINGS

FIG. 1 is an axial cross-section of the preferred embodiment of wetness sensor according to the invention;

FIG. 2 is an axial cross-section taken at line 2—2 in FIG. 1;

FIG. 3 is an end view taken at line 3—3 in FIG. 2; and

FIG. 4 is a schematic circuit drawing.

DETAILED DESCRIPTION OF THE INVENTION

A leak point detector 10 according to the invention is shown in FIGS. 1–3. Its body 11 may have any desired external configuration, from a single cylindrical shape to one which is shaped for a better grip. A passage 12 passes a catheter 13.

The catheter is a tube having an internal lumen 14 through which liquid, usually water or a saline solution, is passed into the bladder. The proximal end 15 of the catheter is connected to a source of liquid (not shown). The distal 16 end of the catheter is passed through the urethra into the bladder. Leakage to be detected will flow between the urethral wall and the external wall 17 of the catheter when the urethra is no longer able to prevent the leakage.

Catheter wall 17 makes a close fit with wall 18 of passage 12 at its proximal end 19. Passage 12 is expanded at the distal end 20 of the body to form a receptacle 21. Drain channels 22 extend from the receptacle to the exterior of the body so as to drain liquid that flows into the receptacle. There is no intention or purpose to collect the liquid, and it must promptly be drained for a reason yet to be disclosed.

A first, reference, thermistor 25 is bonded to the body where it will be exposed to ambient temperature. The bonding material 26 may also encapsulate this thermistor if desired. If so, it must be sufficiently heat conductive as to respond to room temperature. It is not intended to be contacted, by any fluid other than air, and not even that if it is encapsulated.

A second, detector, thermistor 28 is bonded to the wall 29 of the receptacle by a layer 30 of cement. It is exposed so as to be contacted by liquid which has leaked from the patient. It is also exposed to ambient temperature so the two thermistors will produce the same response until the detector thermistor is contacted by leakage fluid, whose temperature is higher than ambient.

In the procedure, the catheter is first passed into the bladder through the urethra. Then the proximal end of the catheter is passed through the passage 12. When it is at a desired location along the catheter, a plunger 31 will be set to bear against the catheter so the body cannot slide along the catheter. The plunger may be spring-driven, threaded, or otherwise mounted as desired for this purpose.

Leads 35 from the reference thermistor 25, and leads 36 from detector thermistor 28 pass to a detector and amplifier circuit 37 powered by a power supply 38. Circuit 37 may be quite simple. A differential amplifier of any type which can detect a difference in the resistance of the thermistors, and produce an output signal in response to the difference in the outputs of the two thermistors will serve. If desired, sensitivity adjustment means may be provided to ignore differences of only a few degrees, when a difference of at larger number degrees will generally exist between the temperature of the leaked liquid and room temperature. This will prevent the instrument from responding to trivial differences in temperature which might be caused by breezes in the room, for example.

The signal from circuit 37 is provided to output indicators 40 ("signal") through a lead 42. The signal may be a light emitting diode for visual indication that a leak has occurred, or a chime or a buzzer for audible indication.

A recorder 41 of any desired type also receives the signal from the amplifier through lead 42. It may cause a mark or any other notation to be made on a chart, which may be accompanied by data from other sources that relate to time, pressure and volume, for example.

A thermistor is given as the preferred example of a temperature sensing element for use in this environment. Its surface is resistant to water and urine, and the device is sensitive to small changes of temperature. Its resistance decreases with increased temperature. However, other temperature sensors, including direct-reading electronic thermometers may be used instead. Therefore the thermistor is referred to generally as a temperature sensitive element, but is the preferred device.

In use, leakage liquid generally first flows slowly, drop-by-drop as shown in the FIG. 1 as drops 50. They flow along the surface of the catheter to the narrow part of the receptacle, where they contact the detector thermistor. Then they flow out through the drain channels so the thermistor can drain dry again and be ready for the next drops. It is undesirable for the detector thermistor to remain in continuous contact with the liquid, because this would frustrate the comparison between the temperature of freshly-received liquid and the ambient temperature, and would prevent intermittent flows from being sensed.

This invention is not to be limited by the embodiment shown in the drawings and described in the description, which is given by way of example and not of limitation, but only in accordance with the scope of the appended claims.

I claim:

1. A leakpoint wetness sensor for urological investigations, comprising:

an instrument body having a passage therethrough to pass a catheter intended for insertion into the bladder through the urethra;

a temperature sensitive reference sensor mounted to the body, exposed to and responsive to ambient temperature;

a receptacle in said body so disposed and arranged as to receive liquid which leaks from the urethra past the catheter;

a temperature sensitive detector sensor mounted to said body where it will be contacted by said leaked liquid, said detector sensor being responsive to the temperature of said liquid;

circuitry responsive to outputs from said sensors to provide a response reflective of a difference between the temperatures when said detector sensor is wetted by said leaked liquid; and signal means responsive to said last-named response to indicate the presence of leaked liquid in the receptacle.

2. Apparatus according to claim 1 in which said detector sensor is disposed in said receptacle.

3. Apparatus according to claim 2 in which drainage channels extend from said receptacle to the outside of said body to drain liquid from the receptacle.

4. Apparatus according to claim 1 in which said circuitry includes a differential amplifier.

5. Apparatus according to claim 1 in which said signal means comprises a visible source.

6. Apparatus according to claim 1 in which said signal means comprises an audible source.

7. Apparatus according to claim 1 in which recorder records related data when wetness is detected.

8. Apparatus according to claim 1 in which said reference sensor and detector sensor are thermistors.

9. Apparatus according to claim 8 in which said detector sensor is disposed in said receptacle, and in which drainage channels extend from said receptacle to the outside of said body to drain liquid from the receptacle.

10. Apparatus according to claim 9 in which said circuit means includes a differential amplifier.

* * * * *